United States Patent
Nikolaev et al.

(10) Patent No.: US 7,910,881 B2
(45) Date of Patent: Mar. 22, 2011

(54) MASS SPECTROMETRY WITH LASER ABLATION

(75) Inventors: Evgenij Nikolaev, Moscow (RU); Jochen Franzen, Bremen (DE)

(73) Assignee: Bruker Daltoniks, GmbH, Bremen (DE)

( * ) Notice: Subject to any disclaimer, the term of this patent is extended or adjusted under 35 U.S.C. 154(b) by 188 days.

(21) Appl. No.: 11/943,904

(22) Filed: Nov. 21, 2007

(65) Prior Publication Data

US 2008/0128614 A1 Jun. 5, 2008

(30) Foreign Application Priority Data

Dec. 4, 2006 (DE) .......................... 10 2006 056 929

(51) Int. Cl.
*H01J 49/16* (2006.01)

(52) U.S. Cl. .................. 250/288; 250/281; 250/282

(58) Field of Classification Search .................. 250/288, 250/281, 282

See application file for complete search history.

(56) References Cited

U.S. PATENT DOCUMENTS

| | | | | |
|---|---|---|---|---|
| 5,174,962 A * | 12/1992 | Brennan | ...................... | 422/78 |
| 5,210,412 A * | 5/1993 | Levis et al. | ................... | 250/288 |
| 5,663,561 A * | 9/1997 | Franzen et al. | ............... | 250/288 |
| 6,515,279 B1 * | 2/2003 | Baykut | ...................... | 250/285 |
| 6,569,324 B1 * | 5/2003 | Moon et al. | ................. | 210/198.2 |
| 6,657,196 B2 * | 12/2003 | Endo et al. | ............... | 250/339.11 |
| 7,193,223 B2 * | 3/2007 | Franzen | ...................... | 250/425 |
| 7,271,397 B2 * | 9/2007 | Bryden et al. | ................. | 250/427 |
| 7,442,922 B2 * | 10/2008 | Knebel et al. | ................. | 250/306 |
| 2004/0041093 A1 * | 3/2004 | Schultz et al. | ................ | 250/288 |
| 2005/0199823 A1 * | 9/2005 | Franzen | ...................... | 250/425 |
| 2005/0247871 A1 | 11/2005 | Bryden et al. | | |
| 2006/0219676 A1 * | 10/2006 | Taylor et al. | ............ | 219/121.69 |
| 2008/0042055 A1 | 2/2008 | Baykut et al. | | |

FOREIGN PATENT DOCUMENTS

DE  10 2006 019 530.2 A1  11/2007

\* cited by examiner

*Primary Examiner* — David A Vanore
*Assistant Examiner* — Michael Maskell
(74) *Attorney, Agent, or Firm* — Law Office of Paul E. Kudirka

(57) ABSTRACT

A mass spectrometric analysis of surface material is performed by vaporizing the surface material with pulses of laser light and then collecting the vaporized material by dissolving it in a liquid. The liquid with the dissolved material is then fed to an ionization process, preferably an electrospray ionization process. The resulting ions are then analyzed with a mass spectrometer. The method is particularly suited for use with imaging mass spectrometry.

10 Claims, 3 Drawing Sheets

MASS SPECTROMETRY WITH LASER ABLATION

BACKGROUND

The invention relates to the mass spectrometric analysis of surface material by means of laser ablation.

The mass spectrometric analysis of material on or in surfaces of solid bodies has many applications, ranging from imaging mass spectrometry of substance distributions in thin tissue sections or thin-layer chromatographic plates to the analysis of arbitrarily applied analytical samples on sample supports. There are many different methods for removing the surface material, some of which also ionize immediately, for example vacuum RF sparks (SSMS="spark source mass spectrometry"), sputtering (SIMS="secondary ion mass spectrometry") or matrix-assisted laser desorption and ionization (MALDI). Other removal methods such as laser ablation only remove neutral molecules of the material being analyzed. The neutral molecules must then be ionized, for example in an inductively coupled plasma (ICP) in which the molecules are broken down into ionized atoms, thus making it possible to determine the elementary composition of the surface material. The method is used to analyze metal atoms in organic material, for example.

In recent years, the focus of attention has been on imaging mass spectrometry (IMS); and particularly matrix-assisted laser desorption (MALDI) is used as the method of removal and ionization. This requires matrix substance to be applied to the sample surface, however. The method, which is particularly successful for thin tissue sections, requires that a relatively thick, very uniform layer of matrix material is applied, by spraying as a solution in individual layers, in order to hold back contaminating substances and transport proteins to the surface. A favorable method for this has been described in the Patent Application DE 10 2006 019 530.2.

This method has the disadvantage, however, that the layer of matrix substance applied limits the lateral spatial resolution to some 200 micrometers at best, even if finer focusing of the desorbing laser beam is achieved. It is therefore not possible to look into individual biological cells and determine the composition of individual organelles, for example.

Other applications of mass spectrometry have already shown that electric near fields, which can be generated in front of the probes of an atomic force microscope (AFM), for example, can be used to produce a near-field focusing of laser beams, thus allowing vaporization pits down to a mere 30 nanometers or so in diameter to be produced. This lateral spatial resolution of around 30 nanometers makes it possible to vaporize a volume with around 10,000 molecules if one assumes an average molecular weight of around 1,000 Daltons. With 100 nanometer vaporization pits, it is possible to vaporize some 300,000 molecules. Such numbers of molecules are very low for mass spectrometric analyses; they require highly effective methods of ionization and ion transfer to the mass analyzer.

SUMMARY

The invention consists in producing a cloud of substances by first vaporizing these substances with a pulse of laser light from a removal site on a surface, preferably in an inert gas, then collecting the cloud by dissolving it in a liquid at a collection site before feeding it solved in the liquid to an ion source. It is preferred if the ion source operates by electrospray ionization. A lens-focused laser beam or a laser beam with near-field focusing can be used for the vaporization. The liquid can be open at the collection site, or be covered by a permeable membrane or a porous cover, so that the vaporized molecules can dissolve out of the cloud. The collection site can be a capillary meniscus at the end of concentric capillaries, for example, or also an open site in liquid chips. In particular, it is possible to control either the supply or the draining of the liquid to/from the collection site, or both. The inert gas can move the cloud with vaporized material toward the collection site. Nano-electrospray ionization with its highly efficient transfer of ions into the vacuum system of the mass spectrometer is particularly suitable for the ionization.

BRIEF DESCRIPTION OF THE DRAWINGS

FIG. 1 shows an open capillary meniscus (6), which requires a form of control for the supply and draining to maintain a constant form. The capillary meniscus (6) is located at the end of two concentric capillaries, the supply (3) being through the outer capillary (1) and the draining (5) through the inner capillary (2). The flow (4) in the interior turns round in front of the meniscus and flows back in the inner capillary.

In FIG. 2 both capillaries (1) and (2) are closed off by an extremely thin membrane (7). The permeable membrane (7), for example a silicone membrane, can remove the substances of the substance cloud and give them to the liquid.

In FIG. 3 the capillaries are closed off by a porous or felt-like disk of material (8), through which the liquid can flow.

FIG. 7 shows a control method which uses a reflected external beam of light generated by a light generator (20) and detected by a detector (21).

In FIG. 8, an internal glass fiber (22) is used to bring light from a combined generator-receiver (23) to the meniscus and back again on reflection.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

Figure 1:
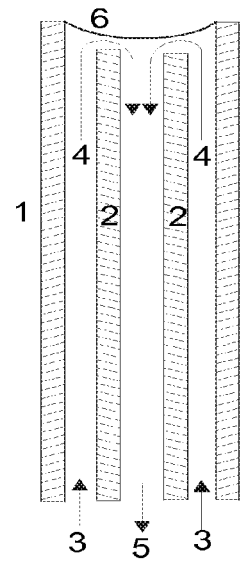
FIGS. 1 to 3 illustrate different embodiments of a collection liquid surface at the end of concentric capillaries for collecting the vaporized materials.
Figure 2:
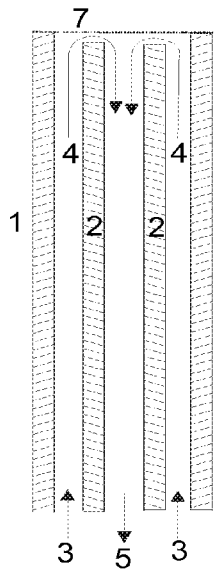
Figure 3:
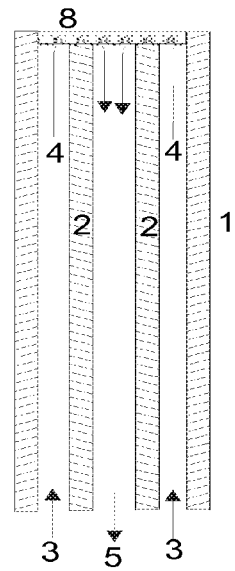
Figure 4:
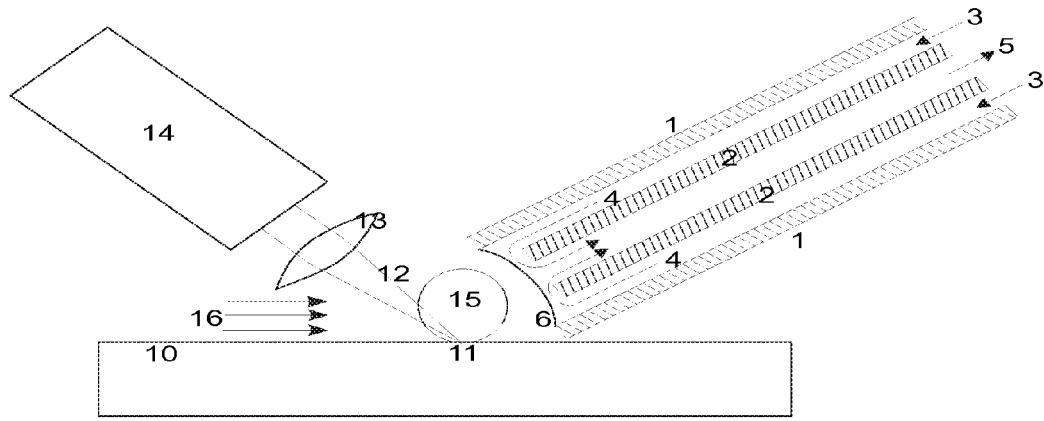
FIG. 4 is a schematic representation of how material from the surface of a solid body (10) is vaporized to a cloud (15) by a pulse of laser light (12) generated in a pulsed laser (14) and focused by a lens (13) onto the point (11). A gentle flow (16) of an inert gas blows the cloud (15) onto the meniscus (6) of a concentric capillary arrangement, as shown in FIG. 1, where it is dissolved.
Figure 9:
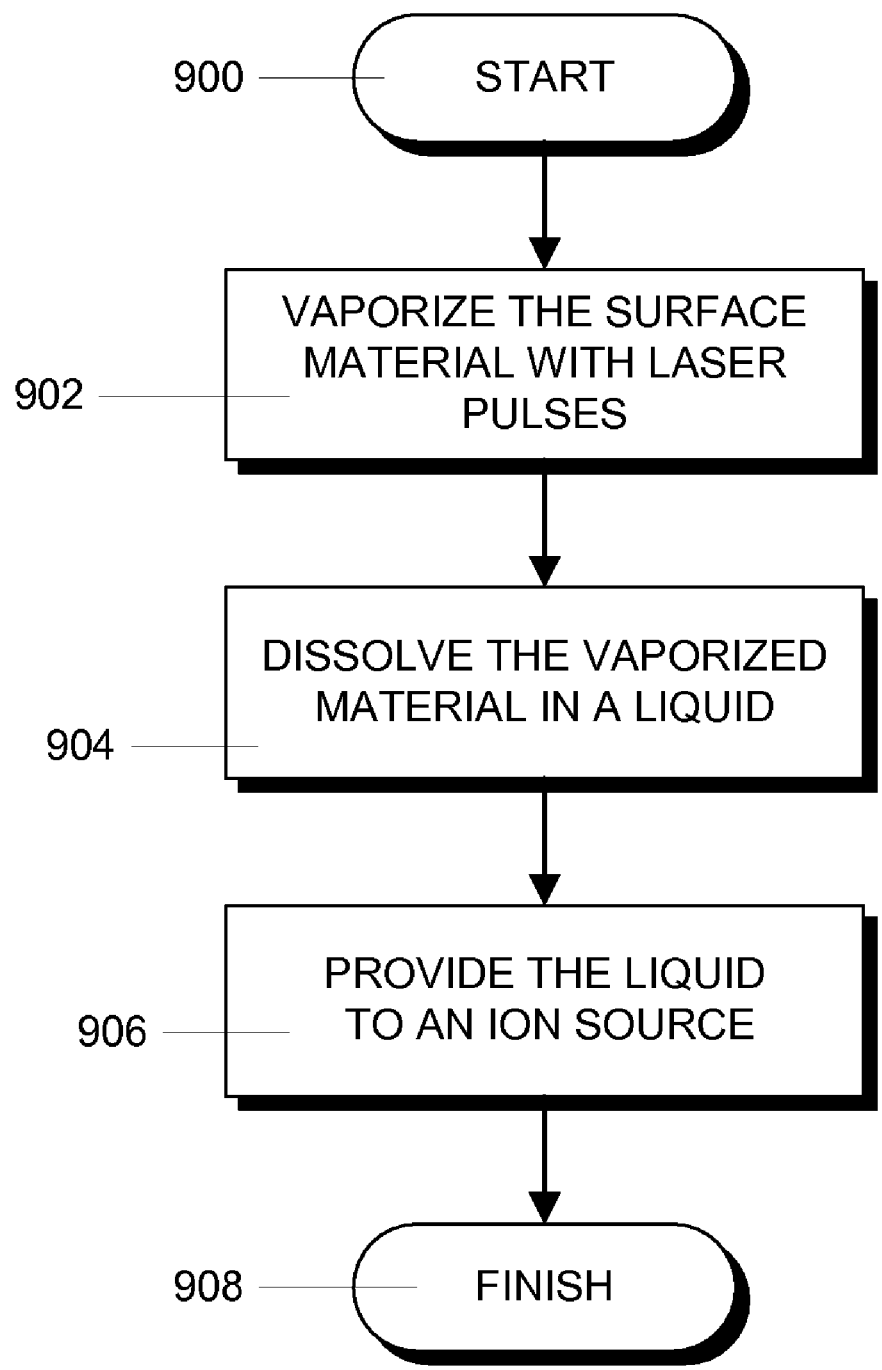
FIG. 9 shows the steps in an illustrative process conducted in accordance with the principles of the invention.

A simple but very effective embodiment is shown as a schematic diagram in FIG. 4 and the steps in the process are shown in FIG. 9. The process begins in step 900 and proceeds to step 902. In step 902, a laser beam pulse (12) from a pulsed laser (14) is focused by a lens of short focal length onto the point (11) and deflagrates material from this spot. The laser can be an infrared laser, a laser in the visible spectrum or, preferably, a UV laser. The temporal length of the pulse of laser light is preferably a few nanoseconds, but considerably longer pulses can also be used. The vaporization preferably takes place at atmospheric pressure in an inert curtain gas, for example in pure nitrogen. In step 904, the vaporization cloud (15) is blown by a gentle flow (16) of the inert gas to a collecting meniscus (6) of a suitable liquid, where the substances of the cloud dissolve. The process of dissolution creates a suction effect so that the whole cloud is dissolved, provided that the molecules of the cloud are in fact soluble in the liquid used. In step 906, the dissolved substances are fed to a nanospray device in the flow of liquid (5). The liquid must be polarizable and have a low viscosity; water with methyl alcohol added is one favorable option. The process then finishes in step 908.

Figure 5:
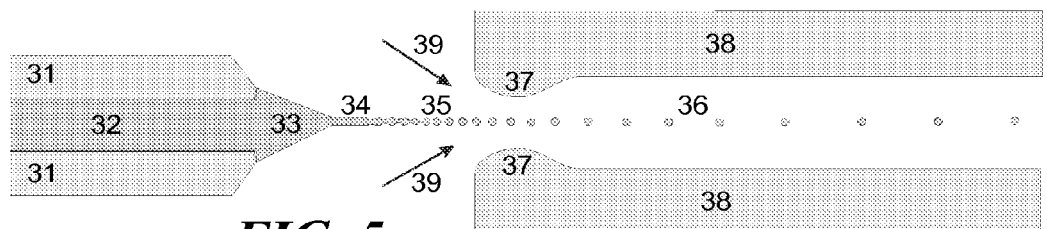
FIG. 5 is a schematic diagram of the nanospraying process: a liquid (32) from a capillary tip (31) is first shaped into a Taylor cone (33) by an electric drawing field, and then drawn out into a thin jet (34), which is broken up into vaporizing droplets (35, 36), and enters a capillary (38) together with inert gas (39) through a nozzle (37), to be transported into the vacuum of a mass spectrometer.
Figure 6:
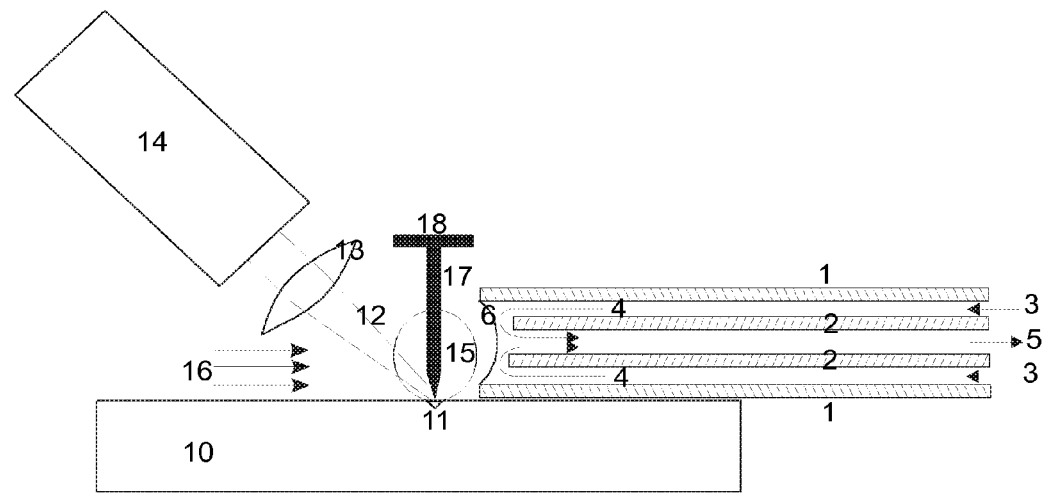
In FIG. 6 the laser beam (12) is focused in the near field of the probe (17) on a cantilever (18) of an atomic force microscope so that the vaporization pit (11) becomes extremely small.
Figure 7:
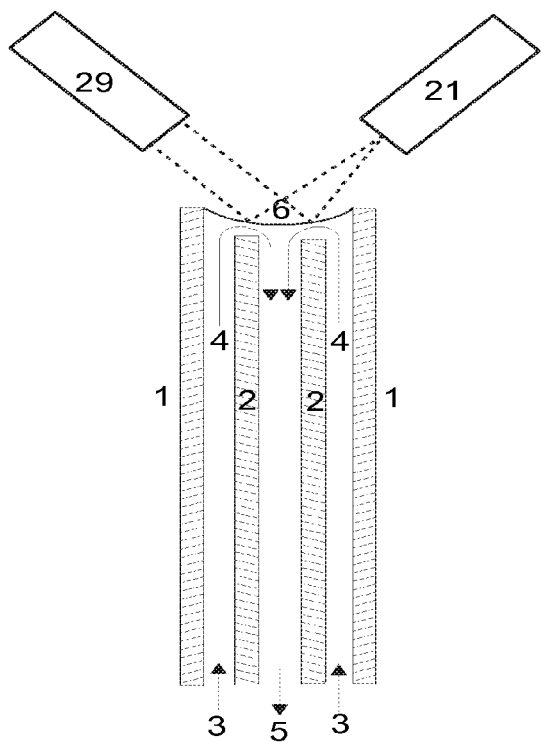
FIGS. 7 and 8 illustrate two principles of meniscus control.
Figure 8:
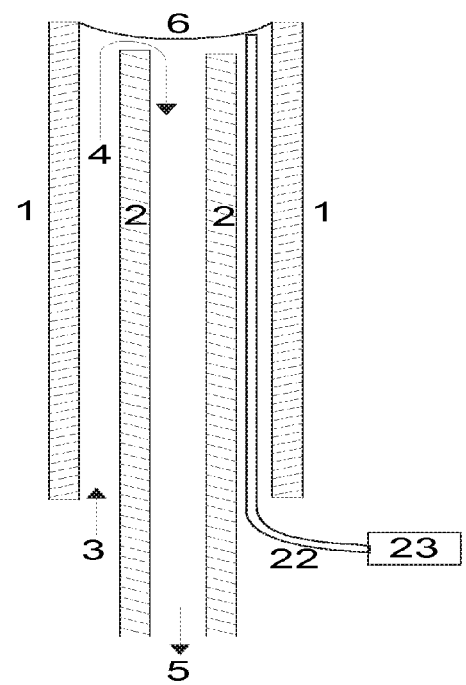

The basic principle of such a nanospray device is shown in FIG. 5. The polarizable liquid (32) containing the dissolved substances of the vaporization cloud is first formed into a Taylor cone (33) by being drawn out of a fine capillary tip (31), whose opening has a diameter of only some 2 to 10 micrometers (preferably between 3 and 5 micrometers) by an electric drawing field with a preferably negative voltage of around 1000 volts. The electric drawing field draws a thin jet of liquid (34) out of this Taylor cone (33). This jet of liquid disintegrates into easily vaporizable droplets (35, 36), each being only some several hundred nanometers in diameter, which enter the entrance capillary (38) of the mass spectrometer together with the inert gas (39), which is fed in, preferably heated. A nozzle (37) can be located at the inlet of the entrance capillary. The droplets are transported in the entrance capillary into the vacuum system of the mass spectrometer being used. The droplets can vaporize in the hot inert gas inside the entrance capillary; or they can fly right into the vacuum system as droplets under the conditions of a Bernoulli focusing in the laminar flow of inert gas, which continuously accelerates the droplets, and vaporize completely only when they arrive in the vacuum system. This way of introducing the substance molecules has a high transfer efficiency because the droplets are continuously focused into the axis.

The process of drawing off the liquid on the polarized surface makes the droplets highly charged; they contain a great many excess protons (if there is a negative attracting voltage). During drying in the hot inert gas, which is sometimes accompanied by a splitting of the droplets, some of the protons are deposited onto the substance molecules, transforming most of them into multiply charged ions. The number of protons per substance molecule depends on the ability of the substance molecules to accept protons, and hence essentially on their size.

The substance ions are fed in the vacuum system to the mass analyzer in the familiar way. The various types of mass analyzer based on RF ion traps, ion cyclotron resonance, time-of-flight measuring devices, quadrupole filters, magnetic sector fields or others can be used. Selected substance ions can also be isolated and fragmented on the way to the mass analyzer in order, for example, to obtain higher identification accuracy.

The open meniscus (6) at the end of the concentric capillaries (or in a collection site on a liquid chip) has to be constantly controlled. The draining can be set within limits using an electric drawing field with variable voltage. The supply is generally controlled by means of a spray pump or a simple pressure control, for example by the height of the liquid level in a supply tank. In order to keep the shape of the meniscus constant, it is necessary to measure the meniscus position, which can be done by optical scanning, for example, as shown in FIG. 7. It can also be done by a reflecting measurement which uses at least one glass fiber in the interior of the concentric capillaries, as shown schematically in FIG. 8.

Instead of vaporization in the lens-focused laser beam, vaporization by means of near-field focusing can also be used, as shown schematically in FIG. 6. Such a near field can be generated by a probe (17) on a cantilever (18) of an atomic force microscope. The tip of this very sharp probe (17) is brought to less than one micrometer from the surface. If the area around the tip is then irradiated with a laser beam, this near-field focusing occurs. With pulsed irradiation it is thus possible to vaporize material from a very small pit. Pit diameters down to around 30 nanometers can be produced. Here too, the material vaporized to a small cloud can be fed to the collection surface by a gentle flow of inert gas. Since the cloud of vaporized material occupies around 1,000 times the volume of the solid substance, a pit 100 nanometers in diameter generates a cloud around one micrometer in diameter, not very homogeneously mixed with a little inert gas. The flow of inert gas must therefore be accurately guided so that it can transport the minute cloud to the collection surface.

The collection area does not necessarily have to be an open liquid surface, however. The liquid can also be covered by a thin membrane, for example, as shown in FIG. 2. The membrane then has to be such that at least a part of the vaporized substances dissolves in it and can permeate through it into the liquid. For many organic substances, the required solubility and permeation is provided in silicone membranes of a suitable degree of polymerization, for example, and is already used as the substance inlet in various branches of mass spectrometry. The permeation of organic substances in the molecular mass range of several hundred Daltons is many orders of magnitude higher than the permeation of nitrogen; this effect is used to introduce these substances into the vacuum system in a way which is favorable in terms of the vacuum system.

It is also possible to cover the collection area with a porous or felt-like cover, the liquid being held in the cover by multiple capillary forces. FIG. 3 illustrates such an arrangement. A piece of filter or blotting paper can be used, for example. The capillary forces in the felt-like cover can be used to automatically control the supply (3) of the liquid from a supply tank, which is under a slight pressure if necessary, in such a way that the surface of the porous cover is always slightly damp.

With knowledge of this invention, the specialist for the respective analytical problems can develop suitable methods of surface analysis, especially for spatially resolved surface analysis.

What is claimed is:

1. A method for mass spectrometric analysis of surface material comprising:

(a) vaporizing the surface material at a removal site by pulses of laser light;

(b) dissolving molecules of vaporized material in a liquid at an collection site; and (c) providing the liquid containing the dissolved molecules to an ion source.

2. The method of claim 1, wherein the liquid at the collection site has an open surface.

3. The method of claim 1, wherein the liquid at the collection site is covered by a permeable membrane.

4. The method of claim 1, wherein the liquid at the collection site is covered by a porous material.

5. The method of one of claims 1-4, wherein step (a) comprises focusing the pulses of laser light onto the removal site by a lens.

6. The method of claim 5, wherein the ion source is an electrospray ion source.

7. The method of claim 6, wherein the electrospray ion source is a nano-electrospray ion source having a capillary and wherein the capillary has an opening with a diameter of 2 to 10 micrometers.

8. The method of one of claims 1-4, wherein step (a) comprises focusing the pulses of laser light onto the removal site by a near field.

9. The method of claim 8, wherein the ion source is an electrospray ion source.

10. The method of claim 9, wherein the electrospray ion source is a nano-electrospray ion source having a capillary and wherein the capillary has an opening with a diameter of 2 to 10 micrometers.

* * * * *